(12) United States Patent
Robl et al.

(10) Patent No.: US 7,390,824 B1
(45) Date of Patent: Jun. 24, 2008

(54) METHOD FOR TREATING DIABETES EMPLOYING AN AP2 INHIBITOR AND COMBINATION

(75) Inventors: Jeffrey A. Robl, Newtown, PA (US); Rex A. Parker, Titusville, NJ (US); Scott A. Biller, Hopewell, NJ (US); Haris Jamil, Newtown, PA (US); Bruce L. Jacobson, Mercerville, NJ (US); Krishna Kodukula, Princeton, NJ (US)

(73) Assignees: Bristol-Myers Squibb Company, Princeton, NJ (US); Pesident and Fellows of Harvard College, Cambridge, MA (US)

( * ) Notice: Subject to any disclaimer, the term of this patent is extended or adjusted under 35 U.S.C. 154(b) by 844 days.

(21) Appl. No.: 09/391,053

(22) Filed: Sep. 7, 1999

(51) Int. Cl.
*A61K 31/42* (2006.01)
*A61K 31/415* (2006.01)
*A61K 31/425* (2006.01)

(52) U.S. Cl. .................. 514/374; 514/376; 514/385; 514/365; 514/369; 514/866

(58) Field of Classification Search .................. 514/330, 514/365, 369, 374, 376, 385, 866
See application file for complete search history.

(56) References Cited

U.S. PATENT DOCUMENTS

| 4,001,228 | A | | 1/1977 | Mattalia |
| 4,051,250 | A | | 9/1977 | Dahm et al. |
| 4,687,777 | A | * | 8/1987 | Meguro et al. ............ 514/342 |
| 5,187,188 | A | | 2/1993 | Meanwell |
| 5,218,124 | A | * | 6/1993 | Failli et al. |
| 5,254,576 | A | | 10/1993 | Romine et al. |
| 5,262,540 | A | | 11/1993 | Meanwell |
| 5,348,969 | A | | 9/1994 | Romine et al. |
| 5,362,879 | A | | 11/1994 | Meanwell |
| 5,380,854 | A | | 1/1995 | Romine et al. |
| 5,403,852 | A | | 4/1995 | Barreau et al. |
| 5,599,770 | A | | 2/1997 | Kubota et al. |

FOREIGN PATENT DOCUMENTS

| FR | 2.1.56.486 | 6/1973 |
| FR | 2.647.676 | 12/1990 |
| RU | 94012067 | 4/1994 |
| WO | WO92/04334 | 3/1992 |
| WO | WO95/17393 | 6/1995 |

OTHER PUBLICATIONS

Hotamisligil, G. S. et al. "Uncoupling of Obesity from Insuline Resistance Through a Targeted Mutation in ap2, the Adipocyte Fatty Acid Binding Protein," Science, vol. 274, Nov. 26, 1996 (1377-1379).*

(Continued)

*Primary Examiner*—Shengjun Wang
(74) *Attorney, Agent, or Firm*—Rosemary M. Miano; Joseph C. Wang

(57) ABSTRACT

A method is provided for treating diabetes and related diseases, especially Type II diabetes, employing an aP2 inhibitor or a combination of an aP2 inhibitor and another antidiabetic agent such as metformin, glyburide, troglitazone and/or insulin.

8 Claims, 1 Drawing Sheet

OTHER PUBLICATIONS

USP Dictionary of USAN and International Drug Names, 1997, pp. 787 and 792.*

Fessenden and Fessenden, Organic Chemistry second Edition, 1982. pp. 26 and 32.*

Sandouk et al. "antidiabetic agent pioglitazone enhance adipocyte differentiation of 3T3-F442A cells," American Journal of Physiology, 1993, vol. 264, No. 6, pp. C1600-C1608.*

Hotamisligil, G.S. et al, "Uncoupling of Obesity from Insulin Resistance Through a Targeted Mutation in aP2, the Adipocyte Fatty Acid Binding Protein", Science, Vo. 274, Nov. 22, 1996, pp. 1377-1379.

Mai, A. et al, "Dihydro(alkylthio)(naphthylmethyl)oxopyrimidines: Novel Non-Nucleoside Reverse Transcriptase Inhibitors of the S-DABO Series", J. Med. Chem., 1997, 40, 1447-1454.

Dialog Alert DBDR928, Jan. 2, 1997, Pharmaprojects No. 5149.

Kleitzien et al., J. Cel.Biochem.Suppl., vol. 15, No. 8, p. 70 (XP002209109) (1991).

Melki et al., J. Lipid Res. vol. 34, No. 9, pp. 1527-1534 (XP001094445) (1991).

Baxa et al., Biochemistry, vol. 28, No. 22, 1989 pp. 8683-8690.

* cited by examiner

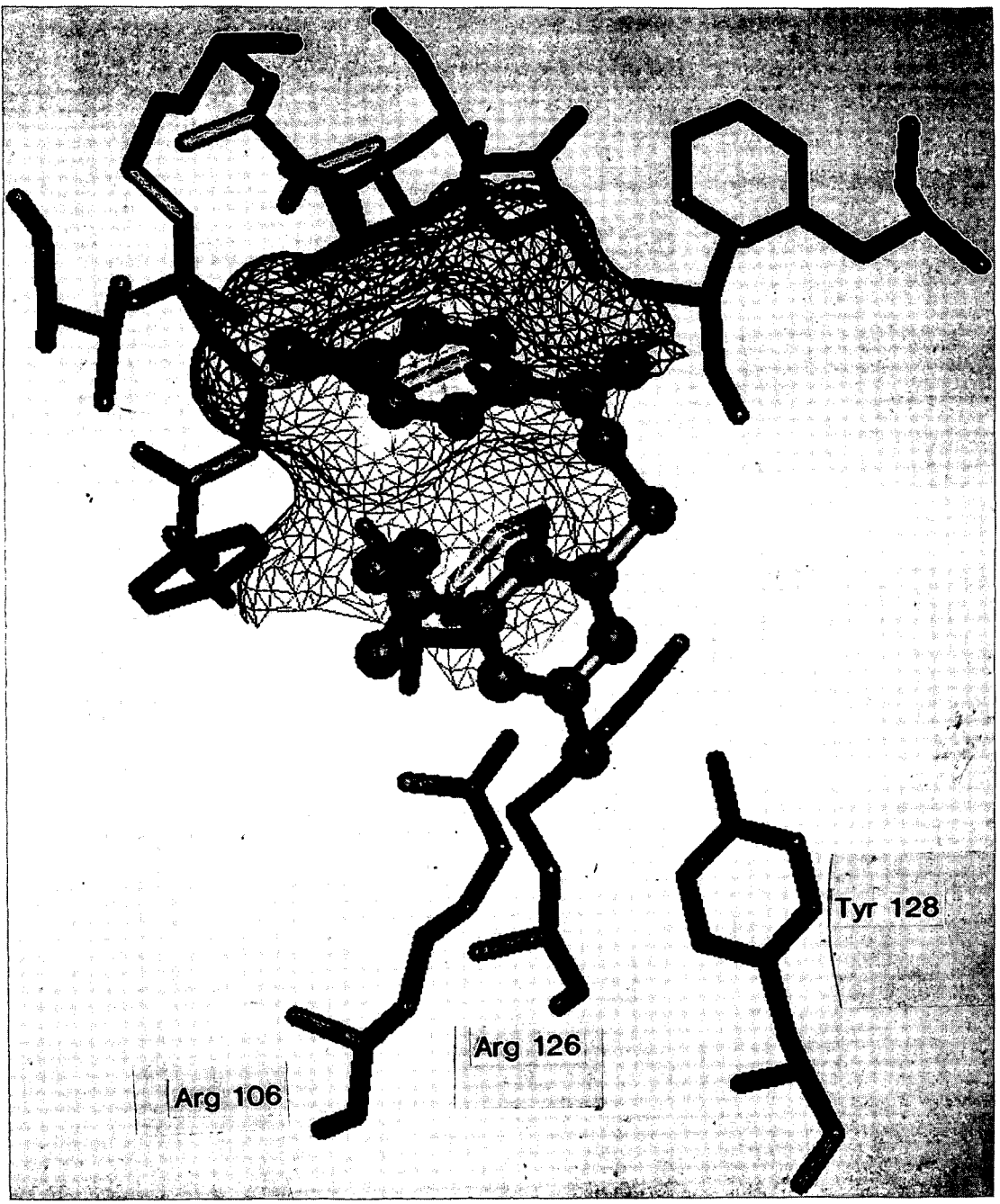
FIGURE

SEQUENCE LISTING

<160> NUMBER OF SEQ ID NOS:  1

<210> SEQ ID NO 1
<211> LENGTH: 132
<212> TYPE: PRT
<213> ORGANISM: HOMO SAPIENS

<400> SEQUENCE: 1

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Val Ile Thr Ile Lys Ser Glu Ser Thr Phe Lys Asn Thr Glu Ile Ser
        50                  55                  60

```
Phe Ile Leu Gly Gln Glu Phe Asp Glu Val Thr Ala Asp Asp Arg Lys
65              70              75                      80

Val Lys Ser Thr Ile Thr Leu Asp Gly Gly Val Leu Val His Val Gln
                85              90                  95

Lys Trp Asp Gly Lys Ser Thr Ile Lys Arg Lys Arg Glu Asp Asp
            100             105                 110

Lys Leu Val Val Glu Cys Val Met Lys Gly Val Thr Ser Thr Arg Val
        115             120                 125

Tyr Glu Arg Ala
    130
```

METHOD FOR TREATING DIABETES EMPLOYING AN AP2 INHIBITOR AND COMBINATION

FIELD OF THE INVENTION

The present invention relates to a method for treating diabetes, especially Type II diabetes, as well as hyperglycemia, hyperinsulinemia, obesity, hypertriglyceridemia and related diseases, employing an aP2 inhibitor alone or in combination with another type antidiabetic agent, and to the combination for use in such method.

BACKGROUND OF THE INVENTION

Fatty acid binding proteins (FABPs) are small cytoplasmic proteins which bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2, an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377-1379, report that aP2-deficient mice placed on a high fat diet for several weeks developed dietary obesity, but, unlike control-mice on a similar diet, did not develop insulin resistance or diabetes. Hotamisligil et al conclude that "aP2 is central to the pathway that links obesity to insulin resistance" (Abstract, page 1377).

DIALOG ALERT DBDR928 dates Jan. 2, 1997, Pharmaprojects No. 5149 (Knight-Ridder Information) discloses that a major drug company "is using virtual screening techniques to identify potential new antidiabetic compounds." It is reported that "the company is screening using aP2, a protein related to adipocyte fatty acid binding protein.",

DESCRIPTION OF THE INVENTION

In accordance with the present invention, a method is provided for treating diabetes, especially Type II diabetes, and related diseases such as insulin resistance, hyperglycemia, hyperinsulinemia, elevated blood levels of fatty acids or glycerol, obesity and hypertriglyceridemia wherein a therapeutically effective amount of a drug which inhibits aP2 (aP2 inhibitor) is administered to a human patient in need of treatment.

In addition, in accordance with the present invention, a method is provided for treating diabetes and related diseases as defined above and hereinafter, wherein a therapeutically effective amount of a combination of an aP2 inhibitor and another type antidiabetic agent is administered to a human patient in need of treatment.

Furthermore, in accordance with the present invention, a novel antidiabetic combination is provided which is formed of a drug which inhibits aP2 and another type antidiabetic agent which functions by a mechanism other than by inhibiting aP2. The aP2 inhibitor will be employed in a weight ratio to the antidiabetic agent (depending upon its mode of operation) within the range from about 0.01:1 to about 100:1, preferably from about 0.5:1 to about 10:1.

The aP2 inhibitors suitable for use in the method of the invention are compounds which bind to the aP2 protein and inhibits its function and/or its ability to bind free fatty acids. The compounds will preferably contain less than 60 carbon atoms, more preferably less than 45 carbon atoms, and will contain less than 20 heteroatoms, more preferably less than 12 heteroatoms. They contain a hydrogen bond donator or acceptor group, preferably acidic in nature, which includes, but is not limited to, $CO_2H$, tetrazole, $SO_3H$, $PO_3H$, $P(R)(O)OH$ (where R is lower alkyl or lower alkoxy), OH, $NHSO_2R'$ or $CONHSO_2R'$ (where R' is lower alkyl), and thiazolidindione, and interacts (directly or through an intervening water molecule), either by ionic or hydrogen bonding interactions, with one, two, or three of the three amino acid residues, designated as Arg 106, Arg 126 and Tyr 128 in human aP2, within the aP2 protein (SEQ ID NO:1).

The compounds suitable for use herein preferably contain an additional substituent, preferably hydrophobic in nature, which include the following groups: alkyl, cycloalkyl, aryl, heteroaryl, cycloheteroalkyl, benzo-fused aryl and heteroaryl, and their substituted counterparts. Especially preferred are aryl and substituted aryl groups. More especially preferred is phenyl and halo or methyl substituted phenyl.

The hydrophobic substituent binds to (in) and/or interacts with a discrete pocket within the aP2 protein (SEQ ID NO:1) defined roughly by the amino acid residues Phe 16, Tyr 19, Met 20, Val 23, Val 25, Ala 33, Phe 57, Thr 74, Ala 75, Asp 76, Arg 78 in human aP2. The through space distance from the hydrogen bond donor/acceptor group and the additional substituent group is within the distance of about 7 to about 15 Angstroms.

The above compounds may be employed in the form of pharmaceutically acceptable salts thereof and prodrug esters thereof.

BRIEF DESCRIPTION OF FIGURE

The accompanying FIGURE is a computer generated image of a partial X-ray structure of compound XVIA (described hereinafter) bound to human aP2.

DETAILED DESCRIPTION OF THE INVENTION

Examples of aP2 inhibitors suitable for use herein include compounds which include an oxazole or analogous ring. Thus, U.S. Pat. No. 5,218,124 to Failli et al (the disclosure of which is incorporated herein by reference) discloses compounds, which have activity as aP2 inhibitors and thus suitable for use herein, which include substituted benzoylbenzene, biphenyl- and 2-oxazole-alkanoic acid derivatives having the following structure:

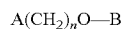

wherein
A is a group having the formula

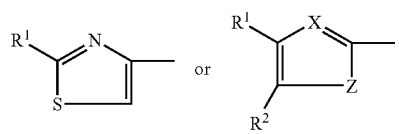

wherein
X is —N— or

Z is

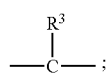

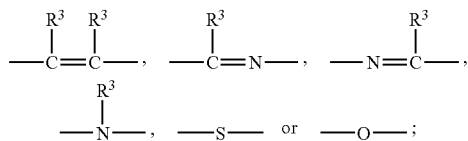

$R^1$ is hydrogen, lower alkyl or phenyl;
$R^2$ is hydrogen or lower alkyl; or
$R^1$ and $R^2$ taken together form a benzene ring, with the proviso that when X is —N—, Z is other than

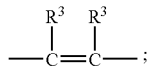

$R^3$ is hydrogen or lower alkyl;
n is 1-2;
B is

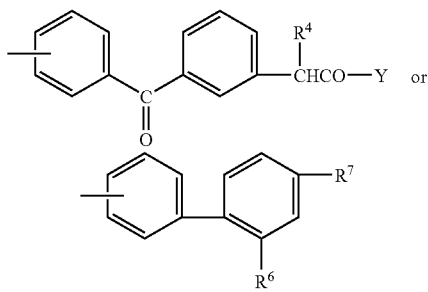

wherein
Y is $OR^5$ or $N(OH)R^8$;
$R^4$ and $R^5$ are each, independently, hydrogen or lower alkyl;
$R^6$ is hydrogen, halo or nitro;
$R^7$ is

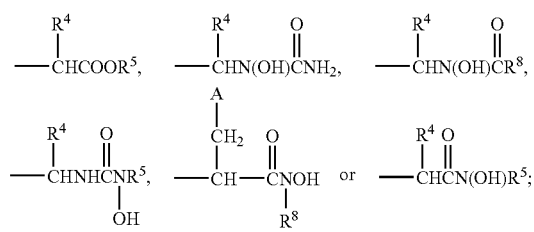

$R^8$ is lower alkyl;

m is 0-3;

and the pharmacologically acceptable salts thereof.

The grouping A embraces, inter alia, 5- or 6-membered unsaturated nitrogen, sulfur or oxygen containing mono- or benzofused-heterocycles, optionally substituted with lower alkyl or phenyl. The foregoing definition embraces the following heterocyclic moieties; furyl, pyrrolyl, thienyl, oxazolyl, thiazolyl, imidazolyl, pyridyl, pyrazinyl, pyrimidinyl, benzofuranyl, benzothienyl, benzothiazolyl, indolyl, benzoxazolyl, quinazolinyl, benzimidazolyl, quinoxalinyl, quinazolinyl and the like.

Preferred are the examples where A is defined as above and B is

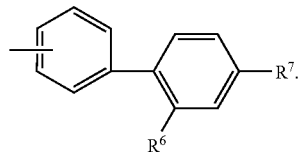

and $R^7$ is

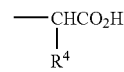

In another embodiment of the present invention, compounds which have activity as aP2 inhibitors suitable for use herein are disclosed in U.S. Pat. No. 5,403,852 to Barreau et al (which is incorporated herein by reference) which are oxazole derivatives and have the structure

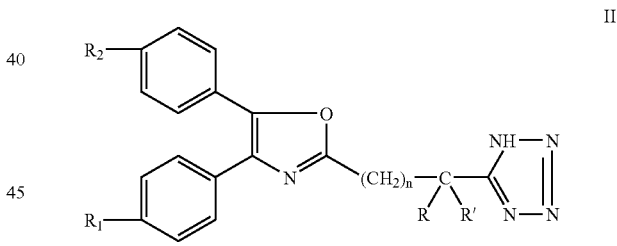

II in which;

R and R' are identical or different and represent a hydrogen atom or an alkyl radical containing 1 or 2 carbon atoms, $R_1$ and $R_2$ are identical or different and represent hydrogen or halogen atoms or alkyloxy radicals in which the alkyl portion contains 1 to 4 carbon atoms in a straight or branched chain, and n equals 3 to 6, as well to their salts, to their isomers where they exist and to pharmaceutical compositions containing them.

In addition, other compounds which have activity as aP2 inhibitors suitable for use in the method of the invention are compounds disclosed in U.S. Pat. No. 4,001,228 to Mattalia (which is incorporated herein by reference) which are 2-thiol-4,5-diphenyloxazole S-derivatives which have the structure

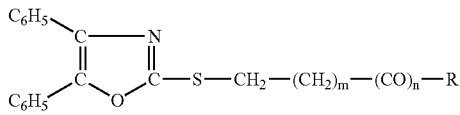

III wherein m is 0, 1 or 2, n1 is 1 and R represents hydroxy, alkoxy or amino. Also included within the scope of this invention are salts of the compounds of formula III above, particularly pharmaceutically acceptable addition salts thereof.

Preferred are S-(4,5-diphenyloxazol-2-yl)-mercaptocarboxylic acids of the formula:

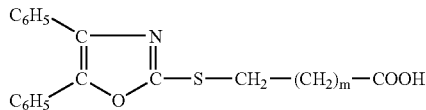

wherein m is 0, 1 or 2, and pharmaceutically acceptable lower alkyl esters and salts thereof.

In another embodiment of the present invention, compounds which have activity as aP2 inhibitors suitable for use herein are disclosed in U.S. Pat. No. 4,051,250 to Dahm et al (the disclosure of which is incorporated herein by reference) which discloses azole derivatives of the structure

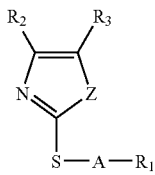

IV wherein $R_1$ is carboxyl, esterified carboxyl or other functionally modified carboxyl group; $R_2$ and $R_3$ each are aryl of up to 10 carbon atoms; A is $C_nH_{2n}$ in which n is an integer from 1 to 10, inclusive; and Z is O or S, and the physiologically acceptable salts thereof.

Preferred are preferred compounds as disclosed in the Dahm et al patent.

In still another embodiment of the invention, compounds which have activity as aP2 inhibitors suitable for ue herein are disclosed in U.S. Pat. No. 5,380,854 to Romine et al (the disclosure of which is incorporated herein by reference) and are phenyl-heterocyclic oxazole derivatives which have the structure

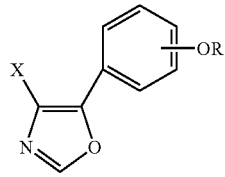

V

X is

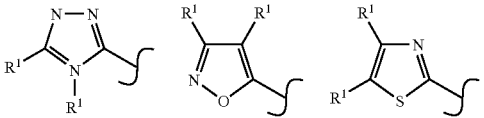

R is $CH_2R^2$;
$R^1$ is Ph or Th;
$R^2$ is

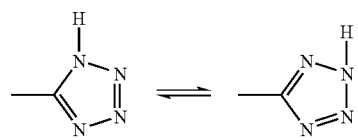

$CO_2R^3$, and
$R^3$ is H, or $C_1$-$C_4$ lower alkyl;

or pharmaceutically acceptable salt thereof.

Preferred are the compounds where R is $CH_2CO_2H$ and

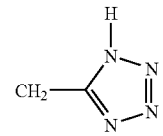

or its tautomer and $R^1$ is Ph.

In yet another embodiment of the method of the invention, compounds which have activity as aP2 inhibitors suitable for use herein are disclosed in PCT application Wo 95/17393 which are diaryloxazole derivatives having the structure

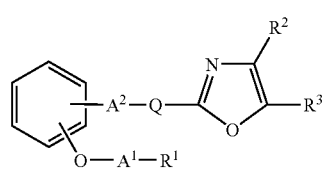

VI wherein $R^1$ is carboxy or protected carboxy,
$R^2$ is aryl which may have suitable substituent(s),
$R^3$ is aryl which may have suitable substituent(s),
$A^1$ is lower alkylene,
$A^2$ is bond or lower alkylene and
—Q— is

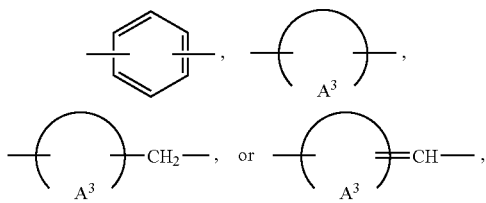

(in which

is cyclo (lower)alkane or cycle(lower)alkene, each of which may have suitable substituent(s)).

Preferred are the preferred compounds of WO 95/17393 as illustrated by the working Examples thereof.

Another embodiment of compounds which have activity as aP2 inhibitors suitable for use herein are disclosed in U.S. Pat. No. 5,362,879 to Meanwell (the disclosure of which is incorporated herein by reference) which are 4,5-diphenyloxazole derivatives having the structures

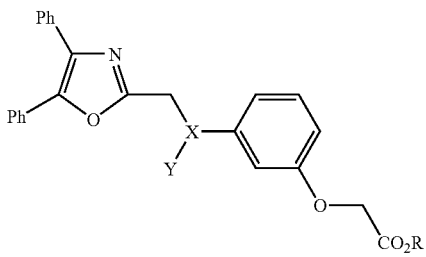

VIIA wherein
R is H or $C_1$-$C_5$ lower alkyl,
X is N or CH,
Y is H or $CO_2R^1$, or $COR^2$,
$R^1$ is $C_1$-$C_5$ lower alkyl, or phenylmethyl, and
$R^2$ is $C_1$-$C_5$ alkyl;

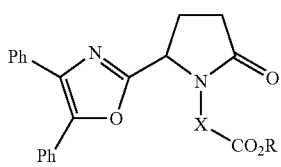

VIIB wherein
R is H or $C_1$-$C_5$ lower alkyl,
X is $(CH_2)_n$ or para or meta substituted phenyl
wherein the substituent is $OR^2$,
$R^2$ is $C_1$-$C_5$ alkyl, and
n is an integer of 4 to 8, and pharmaceutically acceptable salts thereof.

Preferred are the preferred compounds of the Meanwell patent as illustrated by the working Examples thereof.

In still another embodiment of the present invention, compounds which have activity as aP2 inhibitors suitable for use herein are disclosed in U.S. Pat. No. 5,187,188 to Meanwell (the disclosure of which is incorporated herein by reference) which are oxazole carboxylic acid derivatives having the structure

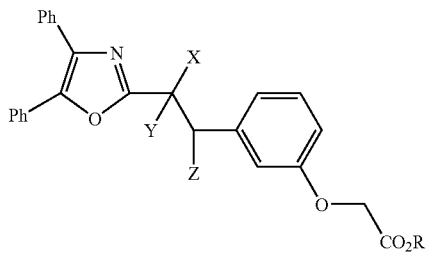

VIII wherein
Y and Z are independently hydrogen or together form a bond;
X is CN, $CO_2R^1$ or $CONR^2R^3$;
R and $R^1$ are independently or together H, Na, or $C_1$-$C_5$ lower alkyl;
$R^2$ and $R^3$ are independently or together H, or $C_1$-$C_5$ lower alkyl;
or alkali metal salt thereof.

Preferred are the preferred compounds of the above Meanwell patent as illustrated by the working Examples thereof.

In another embodiment of the invention, compounds which have activity as aP2 inhibitors suitable for use herein are disclosed in U.S. Pat. No. 5,348,969 to Romine et al (the disclosure of which is incorporated herein by reference) which are phenyloxazolyloxazole derivatives having the structure

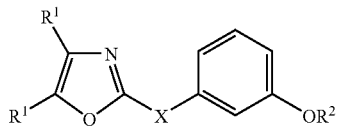

IX wherein
X is

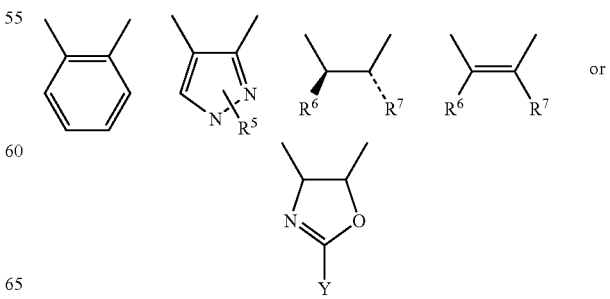

Y is CH$_3$, Ph, or OH, provided that when Y is OH, the compound exists in the keto-enol tautaumerism form

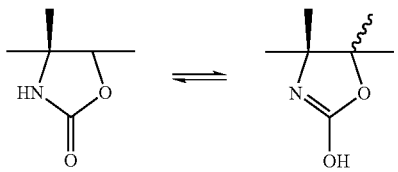

R$^1$ is Ph or Th;
R$^2$ is CH$_2$R$^3$;
R$^3$ is CO$_2$R$^4$;
R$^4$ is H or C$_1$-C$_5$ lower alkyl;
R$^5$ is H or CH$_3$; R$^6$ is OHCHN or H$_2$N; and
R$^7$ is H or OH;

or pharmaceutically acceptable salt thereof.

Preferred are the preferred compounds as delineated in the Romine et al patent and in the working Examples thereof, especially where X is

and R$^2$ is CH$_2$CO$_2$H.

In addition, compounds which have activity as aP2 inhibitors which may be employed herein include those disclosed in U.S. Pat. No. 5,262,540 to Meanwell. (the disclosure of which is incorporated herein by reference) and are 2-(4,5-diaryl)-2-oxazolyl substituted phenoxyalkanoic acids and esters having the strucutre

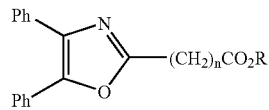   XA

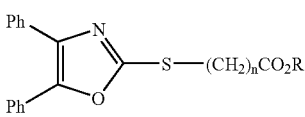   XB (wherein n is 7-9 and R is hydrogen or lower alkyl; or when R is hydrogen, the alkali metal salt thereof),

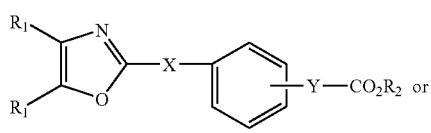   XC

-continued

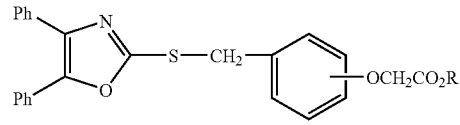   XD wherein
R$_1$ is phenyl or thienyl;
R$_2$ is hydrogen, lower alkyl or together with CO$_2$ is tetrazol-1-yl;
X is a divalent connecting group selected from the group consisting of CH$_2$CH$_2$, CH═CH, and CH$_2$O;
Y is a divalent connecting group attached to the 3- or 4-phenyl position selected from the group consisting of OCH$_2$, CH$_2$CH$_2$ and CH═CH,
or when R$_2$ is hydrogen, an alkali metal salt thereof.

Preferred are the preferred compounds as set out in the above Meanwell et al patent as illustrated in the working Examples thereof.

In another embodiment of the invention, compounds which have activity as aP2 inhibitors suitable for use herein are disclosed in PCT application WO 92/04334 which are substituted 4,5-diaryl heterocycles having the formula

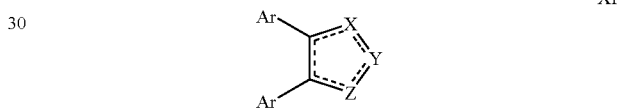   XI in which
each group Ar is the same or different and is optionally substituted phenyl or optionally substituted heteroaryl;
X is nitrogen or CR$^1$;
Y is nitrogen, N(CH$_2$)$_n$A or C(CH$_2$)$_n$A;
Z is nitrogen, oxygen or N(CH$_2$)$_n$A, and the dotted line indicates the optional presence of a double bond so as to form a fully unsaturated heterocyclic ring;
R$^1$ is hydrogen, C$_{1-4}$alkyl, optionally substituted phenyl or optionally substituted heteroaryl;
n is 4 to 12; and
A is CO$_2$H or a group hydrolysable to CO$_2$H, 5-tetrazolyl, SO$_3$H, P(O) (OR)$_2$, P(O) (OH)$_2$, or P(O) (R) (OR) in which R is hydrogen or C$_{1-4}$alkyl, or a pharmaceutically acceptable salt thereof.

Preferred are preferred compounds of WO 92/04334.

In yet another embodiment of the invention, compounds which have activity as aP2 inhibitors suitable for use herein are disclosed in French Patent 2156486 which have the structure

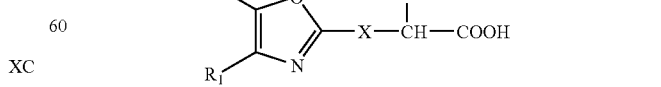   XII

Where X is O or S;
R$_1$ is H, phenyl or phenyl substituted with F, Cl or Br or alkoxy, $R_2$ is H, alkyl, phenyl or phenyl substituted with F, Cl or Br or alkoxy, and $R_3$ is H or alkyl.

Preferred are those preferred compounds as set out in French Patent No. 2156486.

Most preferred oxazole compounds as aP2 inhibitors are the compounds

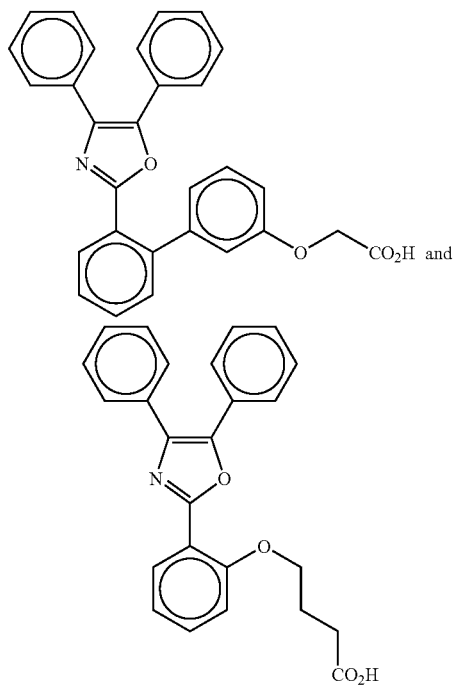

and

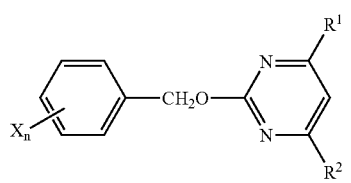

which may be prepared as disclosed in U.S. Pat. No. 5,348,969 to Romine et al.

Another class of aP2 inhibitors suitable for use in the method of the invention include/pyrimidine, derivatives. Thus, U.S. Pat. No. 5,599,770 to Kubota et al (the disclosure of which is incorporated herein by reference) disclose compounds which have activity as aP2 inhibitors and thus suitable for use herein include 2-benzyloxypyrimidine derivatives having the following structure

XIII wherein $R^1$ and $R^2$ are each independently H a halogen, hydroxyl, $C_1$-$C_4$ alkyl, $C_1$-$C_4$ haloalkyl, $C_3$-$C_5$ alkenyl, $C_3$-$C_5$ alkynyl, $C_1$-$C_4$ alkoxy, $C_1$-$C_4$ haloalkoxy, $C_3$-$C_5$ alkenyloxy, $C_3$-$C_5$ alkynyloxy, $C_1$-$C_4$ alkylthio, or phenyl, with the proviso that at least one of $R^1$ and $R^2$ must be hydroxyl;

n is an integer of 0 to 5; and each X which may be identical or different if n is greater than 1 is a halogen, $C_1$-$C_4$ alkyl, $C_1$-$C_4$ haloalkyl, $C_1$-$C_4$ alkoxy, $C_1$-$C_4$ alkylthio, $C_7$-$C_9$ aralkyloxy, phenyl, hydroxymethyl, hydroxycarbonyl, $C_1$-$C_4$ alkoxycarbonyl, or nitro.

Preferred are the compounds in which either $R^1$ or $R^2$ is hydroxyl and the other $R^1$ or $R^2$ is $C_1$-$C_4$ alkyl and X is halogen.

In another embodiment of the method of the invention, compounds which have activity as aP2 inhibitors suitable for use herein are disclosed in A. Mai et al "Dihydro(alkylthio)-(naphthylmethyl)oxopyrimidines: Novel Non-Nucleoside Reverse Transcriptase Inhibitors of the S-DABO Series", J. Med. Chem., 1997, 40, 1447-1454 which have the structures

XIVA

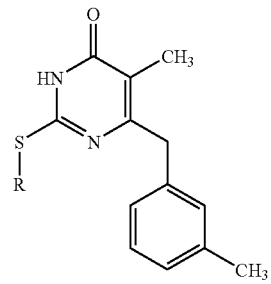

3a R = sec-butyl
3b R = cyclopentyl
3c R = cyclohexyl

XIVB

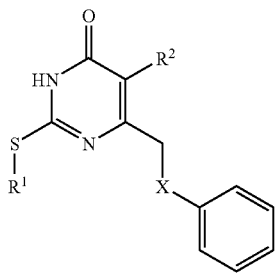

5 X = $CH_2$
6 X = O
7 X = S

XIVC

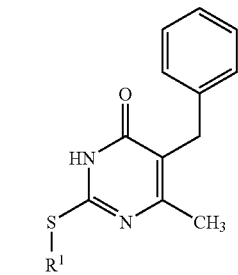

XIVD

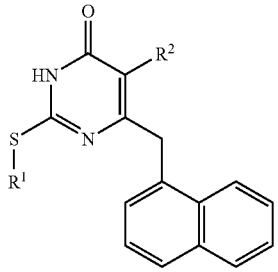

-continued

XIVE

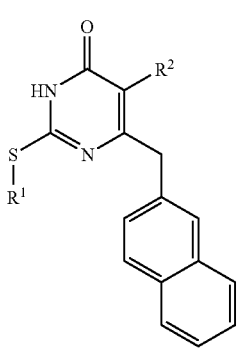

R¹=sec-butyl, cyclopentyl, cyclohexyl;

R²=H, CH₃. The structures XIVA-XIVE are depicted in their keto form. However, it will be apparent to one skilled in the art that they may also exist in their enol form to give structures of the type

XIVF

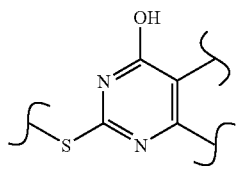

In yet another embodiment of the method of the invention, compounds which have activity as aP2 inhibitors suitable for use herein are disclosed in PCT application WO 96/35678 which are α-substituted pyrimidine-thioalkyl and alkylether compounds which have the structure

XVI

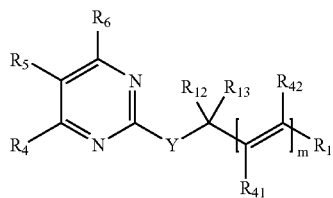

where m is 0 or 1;

$R_1$ is selected from —CO₂$R_{53}$, —CON$R_{54}R_{55}$,

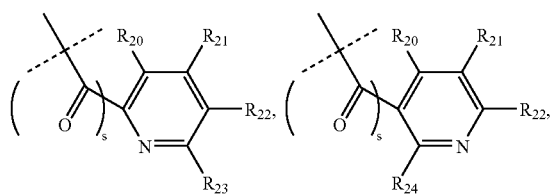

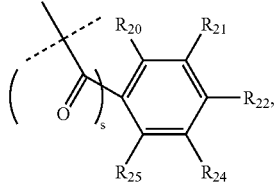

where s is 0 or 1, and $R_{20}$, $R_{21}$, $R_{22}$, $R_{23}$, $R_{24}$, and $R_{25}$ are the same or different and are selected from —H, $C_1$-$C_6$ alkyl, $C_1$-$C_6$ alkenyl, $C_1$-$C_6$ alkoxy, $C_1$-$C_6$ alkylthio, $C_3$-$C_8$ cycloalkyl, —CF₃, —NO₂, -halo, —OH, —CN, phenyl, phenylthio, -styryl, —CO₂($R_{31}$), —CON($R_{31}$)($R_{32}$), —CO($R_{31}$), —(CH₂)$_n$—N($R_{31}$) ($R_{32}$), —C(QH)($R_{31}$ ($R_{33}$), —(CH₂)$_n$N ($R_{31}$)(CO($R_{33}$)), (CH₂)$_n$N($R_{31}$)(SO₂ ($R_{33}$)), or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$-$C_6$ alkyl, $C_1$-$C_6$ alkoxy, —OH, —CH₂OH, —(CH₂)—N($R_{31}$)($R_{32}$), —$C_3$-$C_8$ cycloalkyl, —CF₃, -halo, CO₂($R_{31}$), —CON($R_{31}$) ($R_{32}$), —CO($R_{31}$), —(CH₂)$_n$N($R_{31}$)(CO($R_{33}$)), —(CH₂)$_n$N ($R_{31}$)(SO₂ ($R_{33}$)), —CN, —CH₂CF₃ or —CH(CF₃)₂, or phenyl and the saturated ring may be optionally substituted with 1, 2 or 3, —$C_1$-$C_6$ alkyl, —$C_1$-$C_6$ alkoxy, —OH, —CH₂OH or —(CH₂)$_n$—N($R_{31}$) ($R_{32}$) or one oxo (=O);

where n is 0-3 and $R_{31}$, $R_{32}$ and $R_{33}$ are the same or different and are selected from
—H,
$C_1$-$C_6$ alkyl,
phenyl optionally substituted with 1, 2 or 3-halo, $C_1$-$C_6$ alkyl, $C_1$-$C_6$ alkoxy, —CF₃, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$-$C_6$alkyl)piperazinyl, or a member selected from:
1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazol[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl;
where $R_{53}$ is selected from —H, $C_1$-$C_6$alkyl, $C_3$-$C_6$cycloalkyl, phenyl (optionally substituted with 1, 2, or 3-halo, $C_1$-$C_6$ alkyl, $C_1$-$C_6$ alkoxy, —CF₃, —OH, —CN), or a five or six-membered unsaturated ring containing 0 or 1 oxygen, nitrogen or sulfur, where the unsaturated ring may be optionally substituted with —H, $C_1$-$C_6$ alkyl, $C_1$-$C_6$ alkoxy, —OH, —CH₂OH, or (CH₂)$_n$—N($R_{31}$)($R_{32}$);
where $R_{54}$ and $R_{55}$ being the same or different are selected from —H, $C_1$-$C_6$ alkyl, allyl, or phenyl (optionally substituted with 1, 2 or 3-halo, $C_1$-$C_6$ alkyl, $C_1$-$C_6$ alkoxy- or —$CF_3$), or taken together with the attached nitrogen to form a ring selected from -pyrrolidinyl, -piperidinyl, -4-morpholinyl, -4-thiomorpholinyl, -4-piperazinyl, -4-(1-$C_1$-$C_6$alkyl) piperazinyl;

$R_{41}$ and $R_{42}$, being the same or different, are selected from —H and $C_1$-$C_4$ alkyl;

$R_{12}$ is selected from —H, $C_1$-$C_6$ alkyl, —$C_3$-$C_6$ cycloalkyl, —CN, —C(O)NH$_2$, —C(O)N($C_1$-$C_6$alkyl)($C_1$-$C_6$alkyl), —CO$_2$H, —CO$_2$ ($C_1$-$C_6$alkyl), —CH$_2$OH, —CH$_2$NH$_2$ or —CF$_3$;

$R_{13}$ is selected from —H, $C_1$-$C_6$ alkyl or —CF$_3$;

Y is selected from —S—, —S(O)—, —S(O)$_2$, or —O—;

$R_4$ is —OH;

$R_5$ is selected from —H, —$C_2H_4$OH, —$C_2H_4$—O-TBDMS, halo, —$C_3$-$C_6$ cycloalkyl, $C_1$-$C_3$ alkoxy, —CH$_2$CH$_2$Cl or $C_1$-$C_4$ alkyl, with the proviso that $R_5$ is not isobutyl;

or, when $R_6$ is hydroxyl, $R_4$ and $R_5$ are taken together to form a five or six-memebered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-d]pyrimidine, 5,6-dihydro-furo[2,3-d]pyrimidine, thieno[2,3-d]pyrimidine, 5,6-dihydro-thieno[2,3-d]pyrimidine, 1H-pyrazolo[3,4-d]pyrimidine, 1H-purine, pyrimido[4,5-d]pyrimidine, pteridine, pyrido[2,3-d]pyrimidine, or quinazoline, where the unsaturated ring may be optionally substituted with 1, 2 or 3, $C_1$-$C_6$ alkyl $C_1$-$C_6$ alkoxy, —OH, —CH$_2$OH, or —(CH$_2$)$_n$—N($R_{31}$)($R_{32}$), —$C_3$-$C_8$ cycloalkyl, —CF$_3$, -halo, —CO$_2$ ($R_{31}$), —CON($R_{31}$)($R_{32}$), —CO($R_{31}$), —(CH$_2$)$_n$N($R_{31}$)(CO ($R_{33}$)), —(CH$_2$)$_n$N($R_{31}$)(SO$_2$ ($R_{33}$)), and the saturated ring may be optionally substituted with 1, 2 or 3, —$C_1$-$C_6$ alkyl, $C_1$-$C_6$ alkoxy, —OH, —CH$_2$OH, or —(CH$_2$)$_n$—N($R_{31}$) ($R_{32}$) or one oxo (=O); and $R_6$ is selected from —H, —OH, halo, —CN, —CF$_3$, —O$_2$ ($R_{61}$), —C(O)$R_{61}$ or —C(O)N($R_{61}$)($R_{62}$) where $R_{61}$ and $R_{62}$ are the same or different and are selected from

—H, $C_1$-$C_6$ alkyl, phenyl optionally substituted with 1, 2 or 3-halo, $C_1$-$C_6$ alkyl, $C_1$-$C_6$ alkoxy, —CF$_3$, —OH, —CN, or where $R_{61}$ and $R_{62}$ taken together with the attached nitrogen to form a ring selected from -pyrrolidinyl, -piperidinyl, -4-morpholinyl, -4-thiomorpholinyl, -4-piperazinyl, or -4-($C_1$-$C_6$ alkyl)piperazinyl; or pharmaceutically acceptable salts, hydrates, N-oxides and solvates thereof.

A preferred embodiment is pyrimidine-thioalkyl and alkylether, where $R_4$ is —OH; and $R_6$ is selected from —H, halo, —CN, —CF$_3$, —CO$_2$($R_{16}$), —C(O)$R_{61}$ or —C(O)N($R_{61}$)($R_{62}$), preferably CF$_3$.

A preferred embodiment are compounds of Formula XVI where s is 0 or 1, and Y is —S— or O; more preferably Y is —S—.

Preferred are pyrimidine derivatives of the structures

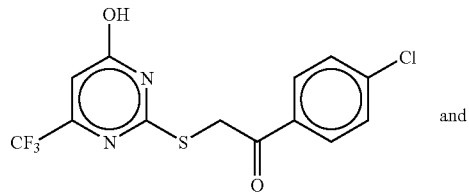

and

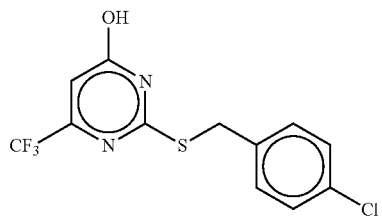

which may be prepared as disclosed in WO 96/35678.

Another embodiment of the method of the invention includes use of aP2 inhibitors which are pyridazinone derivatives. French Patent No. 2,647,676 discloses compounds which have activity as aP2 inhibitors and thus suitable for use herein which have the structures

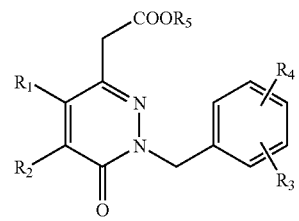

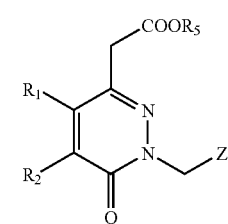

where $R_1$ and $R_2$ are H, alkyl, aryl or arylalkyl, where the alkyl can include as substituents halogen, CF$_3$, CH$_3$O, CH$_3$S, NO$_2$, or $R_1$ and $R_2$ with the carbons to which they are attached can form methylenedioxy, or $R_1$ and $R_2$ can form a $C_3$-$C_7$ non-aromatic ring, or a heterocycle which can be pyridine, pyrazine, pyrimidine, pyridazine, indol, or pyrazole, or an oxygen containing heterocycle which can be pyran or furan, or a sulfur containing heterocycle which can be thiopyran, or thiophene; the heterocycles being optionally substituted with halogen or alkyl, $R_3$ and $R_4$ are H, alkyl, halogen, CF$_3$, CH$_3$O, CH$_3$S or NO$_2$ or $R_3$ and $R_4$ with the carbons to which they are attached can form a methylenedioxy group, $R_5$ is H, and Z is a heterocycle which can be pyridine, thiazole, benzothiazole, benzimidazole or quinoline, which Z group can optionally be substituted with halogen or alkyl.

The preferred pyridazinone derivative is

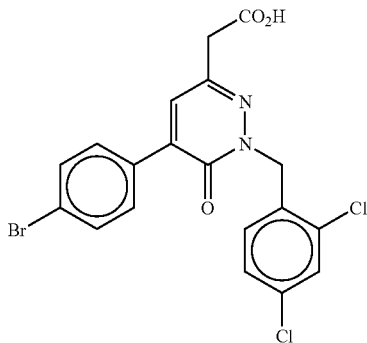

which may be prepared as disclosed in French Patent No. 2,647,676.

Preferred aP2 inhibitors for use herein will include an oxazole ring.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl; isobutyl, pentyl, hexyl, isohexyl, heptyl, 414-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

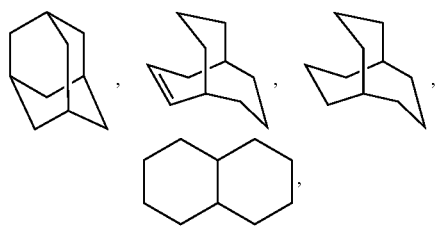

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio.

Unless otherwise indicated the term "aryl" or "Ar" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, 3 or 4 groups selected from hydrogen, halo, haloalkyl, alkyl, haloalkyl, alkoxy, haloalkoxy, alkenyl, trifluoromethyl, trifluoromethoxy, alkynyl, dycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl.

Unless otherwise indicated the term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

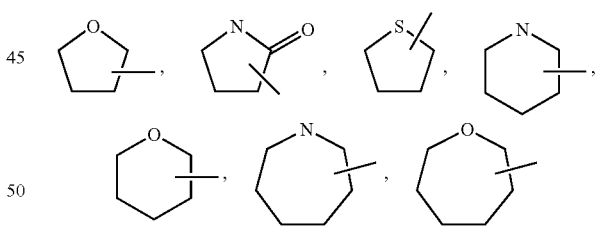

and the like. The above groups may include 1 to 3 substituents such as any of the substituents for alkyl or aryl as defined above. In addition, any of the above rings can be fused to 1 or 2 cycloalkyl, aryl, heteroaryl or cycloheteroalkyl rings.

Unless otherwise indicated, the term "heteroaryl" (also referred to as heteroaryl) as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), linked through a carbon atom or a heteroatom, where possible, optionally via the linker $(CH_2)_p$ (which is defined above), such as

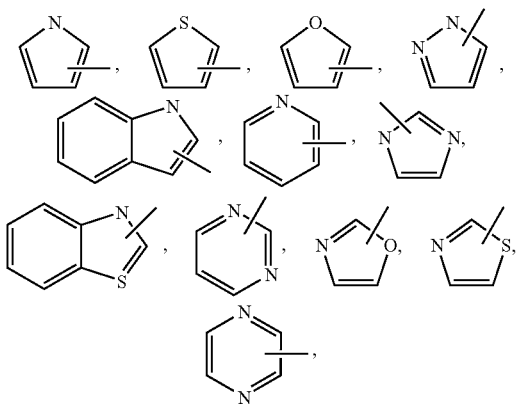

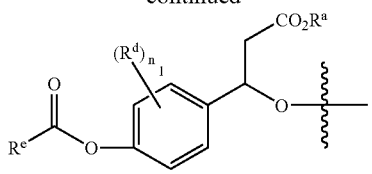

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2; or and the like.

The heteroaryl groups including the above groups may optionally include 1 to 4 substituents such as any of the substituents listed for aryl. In addition, any of the above rings can be fused "to a cycloalkyl, ar"yl, heteroaryl or cycloheteroalkyl ring.

The term "prodrug esters" as employed herein includes prodrug esters which are known in the art for both phosphorus and carboxylic acids such as similar carboxylic acid esters such as methyl, ethyl benzyl and the like. Other examples include the following groups: (1-alkanoyloxy)alkyl such as,

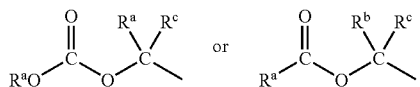

wherein $R^a$, $R^b$ and $R^c$ are H, alkyl, aryl or aryl-alkyl; however $R^aO$ cannot be HO. Examples of such prodrug esters include

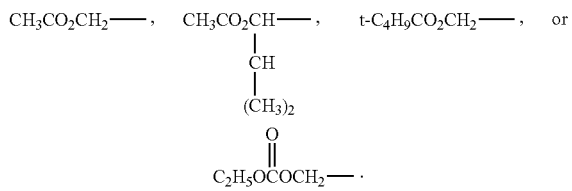

Other examples of suitable prodrug esters include

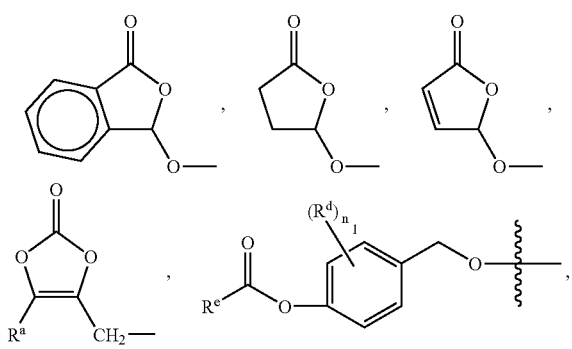

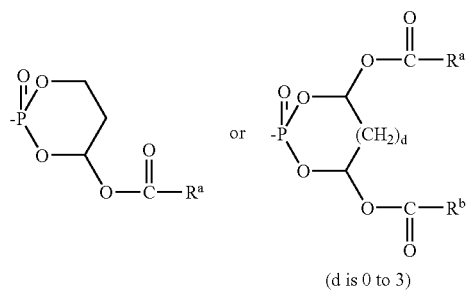

(d is 0 to 3)

Where the aP2 inhibitor is in acid form it may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, ethylenediamine, t-butylamine, t-octylamine, dehydroabietylamine.

Where desired, the aP2 inhibitor may be used in combination with another antidiabetic agent (also referred to herein as "another antihyperglycemic agent") which may be administered orally in the same dosage form in accordance with the invention, a separate oral dosage form or by injection.

The other antidiabetic agent may be a biguanide, a sulfonyl urea, a glucosidase inhibitor, a thiazolidinedione, an insulin sensitizer, a glucagon-like peptide-1 (GLP-1), insulin or a PPAR α/γ dual agonist.

It is believed that the use of the aP2 inhibitor in combination with another antidiabetic agent produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof.

Where the other antidiabetic agent is a biguanide, the aP2 inhibitor will be employed in a weight ratio to biguanide within the range from about 0.01:1 to about 100:1, preferably from about 0.5:1 to about 2:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide being preferred.

The aP2 inhibitor will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904, 769) or miglitol (disclosed in U.S. Pat. No. 4,639,436), which may be administered in a separate oral dosage form.

The aP2 inhibitor will be employed in a weight ratio to the glucosidase inhibitor within the range from about 0.01:1 to about 100:1, preferably from about 0.5:1 to about 50:1.

The aP2 inhibitor may be employed in combination with a thiazolidinedione oral antidiabetic agent or other insulin sensitizers (which has an insulin sensitivity effect in NIDDM patients) such as troglitazone (Warner-Labert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglltazone (CP-86325, Pfizer).

The aP2 inhibitor will be employed in a weight ratio to the thiazolidinedione in an amount within the range from about 0.01:1 to about 100:1, preferably from about 0.5:1 to about 5:1.

The sulfonyl urea and thiazolidinedione in amounts of less than about 150 mg oral antidiabetic agent may be incorporated in a single tablet with the aP2 inhibitor.

The aP2 inhibitor may also be employed in combination with a non-oral antihyperglycemic agent such as insulin or with glucagon-like peptide-1 (GLP-1) such as GLP-1 (1-36) amide, GLP-1 (7-36) amide, GLP-1 (7-37). (as disclosed in U.S. Pat. No. 5,614,492 to Habener, the disclosure of which is incorporated herein by reference), which may be administered via injection, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin may be employed in formulations as described above and in amounts and dosing as indicated in the Physician's Desk Reference.

Where present, metformin or salt thereof may be employed in amounts within the range from about 500 to about 2000 mg per day which may be administered in single or divided doses one to four times daily.

Where present, the thiazolidinedione antidiabetic agent may be employed in amounts within the range from about 0.01 to about 2000 mg/day which may be administered in single or divided doses one to four times per day.

Where present, insulin may be employed in formulations, amouncs and dosing as indicated by the Physician's Desk Reference.

Where present, GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The aP2 inhibitor may be employed in combination with another antidiabetic agent which may be a PPAR α/γ dual agonist such as an N-benzyldioxothiazolidylbenzamide derivative such as disclosed in WO 96/38428 such as 5-(2,4-dioxothiazolidin-5-ylmethyl)-2-methoxy-N-[4-(trifluoromethyl)benzyl]benzamide (KRP-297), WO 98/05531 (Ligand Pharmaceuticals, Inc.) which discloses 2-(4-[2,4-difluorophenyl]-1-heptylureido) ethyl]phenoxy)-2-methylbutyric acid, and WO 97/25042 and WO96/04260 (SKB) which disclose benzoxazole and pyridine derivatives of the structure

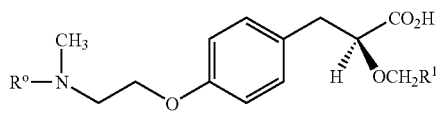

or a pharmaceutically acceptable salt thereof, and/or a pharmaceutically acceptable solvate thereof, wherein $R^o$ represents 2-benzoxazolyl or 2-pyridyl and $R^1$ represents $CH_2OCH_3$ or $CF_3$, such as (S)-3-[4-[2-[N-(2-benzoxazolyl)-N-methylamino)ethoxy]phenyl]-2-(2-methoxy-ethoxy)propanoic acid; or (S)-3-[4-[2-[N-(2-benzoxazolyl)-N-methylamino]-ethoxy]phenyl]-2-(2,2,2-trifluoroethoxy)propanoic acid; or a pharmaceutically acceptable salt thereof, and/or a pharmaceutically acceptable solvate thereof. Dosages employed are as set out in the above references.

The aP2 inhibitor will be employed in a weight ratio to the PPAR α/γ dual agonist within the range from about 0.01:1 to about 100:1, preferably from about 0.5:1 to about 5:1.

Where the aP2 inhibitor is employed in combination with the PPAR α/γ dual agonist, the combination may be employed in an oral dosage form such as a tablet or capsule as will be apparent to one skilled in the art.

In carrying our the method of the invention, a pharmaceutical composition will be employed containing at least one aP2 inhibitor with or without another antidiabetic agent in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1-4 times per day.

A typical capsule for oral administration contains aP2 inhibitor (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of aP2 inhibitor into a vial, aseptically freeze-drying and sealing. For use, the contents of the vial are mixed with 2 mL of physiological saline, to produce an injectable preparation.

Compounds sufficiently satisfying the structural criteria described above may be determined by use of an in vitro assay system which measures the potentiation of inhibition of aP2 by displacement of a fluorescent substrate from aP2 by the inhibitor. Inhibition constants (Ki values) for the inhibitors may be determined by the method described below:

Production of Purified Recombinant Human aP2 Protein

Recombinant human aP2 protein is produced by standard recombinant DNA technology. In the typical case, aP2 is produced by heterologous expression in *E. coli* strain BL21 (D53) transformed with pET11a vector containing the full length human aP2 cDNA (Baxa, C. A., Sha, R. S., Buelt, M. K., Smith, A. J., Matarese, V., Chinander, L. L., Boundy, K. L., and Bernlohr, D. A. (1989). Human adipocyte lipid-binding protein: purification of the protein and cloning of its complementary DNA. Biochemistry 28: 8683-8690 and Xu, Z., Buelt, M. K., Banaszak, L. J., and Bernlohr, D. A. (1991). Expression, purification and crystallization of the adipocyte lipid binding protein. J. Biol. Chem. 266: 14367-14370). Purification of aP2 from *E. coli* is conducted as described by Xu, yielding essentially homogeneous aP2 protein with molecular weight ~14600 daltons and free of endogenous fatty acids. The purified aP2 is capable of binding up to one mole of free fatty acid per mole protein. The binding and structural properties of recombinant aP2 protein were previously shown to be identical to aP2 protein-isolated from adipose tissue.

In Vitro Assay of aP2 Inhibitors

Inhibitors of aP2 are evaluated in a homogeneous fluorescent-based competition assay using recombinant aP2 protein and 1,8-anilino-naphthalene-sulfonic acid (1,8-ANS) as assay substrate. This competition assay was adapted from generalized procedures described previously (Kane, C. D. and Bernlohr, D. A. (1996). A simple assay for intracellular lipid-binding proteins using displacement of 1-anilino-8-sulfonic acid. (1996) Anal. Biochem. 233: 197-204 and Kurian E., Kirk, W. R. and Prendergast, F. G. (1996) Affinity of fatty acid for r-rat intestinal fatty acid binding protein. Biochemistry, 35, 3865-3874). The method relies on the increase in fluorescence quantum yield of 1,8-ANS upon binding to the fatty acid binding site of aP2. The assay is run using appropriate concentrations of inhibitor, 1,8-ANS, and aP2 protein, in order to calculate the inhibitor binding constant (Ki) for compounds being evaluated. The Ki calculation was based on the procedure previously described for calculation of dissociation constants described by Kurian. Lower Ki values indicate higher affinities of compounds binding to aP2.

In the assay as conducted for the inhibitors described herein, a series of aliquots of aP2 (5 µM) in solution in 10 mM potassium phosphate buffer (pH 7.0) are mixed with an equimolar concentration of test compound, followed by the addition of a series of increasing concentrations of 1,8-ANS (from 0 to 5 µM). The assay typically is conducted in 96-well plate format with reagents added using robotic instrumentation (Packard Multiprobe 104). The fluorescence value for each test is determined using a Cytofluor-4000 multi-well fluorescence plate reader (Perceptive Biosystems) using excitation wavelength 360 nm and emission wavelength 460 nm, or using other suitable spectrofluorometer. In preparation for the assay, test compounds are initially prepared at 10 mM in dimethylsulfoxide. All subsequent dilutions and assay additions are made in 10 mM potassium phosphate buffer, pH 7.0.

X-ray crystallography of the inhibitor-aP2 complex can be performed by one skilled in the art using contemporary biophysical methodologies and commercial instrumentation. Such crystallographic data can be used to conclusively determine if a compound used in the present invention has embodied the structural requirement necessary for inhibition of aP2. An example of such an X-ray crystallographic determination is presented below:

Crystals of aP2 complexed with the inhibitors were typically grown by the hanging drop method. aP2, at 8.3 mg/ml, was pre-equilibrated with 1-5 mM of the inhibitor in 0.1 M Tris-HCl pH 8.0, 1% w/v DMSO for four hours. 2 µl drops containing equilibrated protein and reservoir solution at a 1:1 ratio were suspended on plastic cover slips and equilibrated against a 1 ml reservoir containing 2.6-3.0 M ammonium sulfate in 0.1 M Tris-HCl pH 8.0. Crystals typically appeared in 2-3 days and reached maximum size within 2 weeks. Data was typically collected on a single flash-frozen crystal (Oxford Cryosystems) using a Rigaku rotating anode and an R-axis II image plate detector of a Bruker multiwire area detector. Diffraction from aP2 crystals was excellent. Diffraction was consistently observed to better than 2.0 Å resolution often to beyond 1.5 Å resolution. Data was processed either with DENZO/SCALEPACK (R-axis II data), or Xengen (Bruker data). XPLOR was used for structure refinement and model building was done using the molecular modeling package CHAIN. After a single round of refinement, examination of the $F_o$-$F_c$ map typically allowed facile building of the inhibitor into aP2 binding cavity. Iterative fitting and refinement were continued until improvement was no longer seen in the electron density map or R-free.

Referring to the accompanying FIGURE which is a computer generated image of a partial X-ray structure of compound XVIA bound to human aP2, the ball and stick FIGURE in light gray is compound XVIA. The Arg106, Arg126, and Tyr128 residues are depicted as ball and stick figures in dark gray. The dark spheres represent a space filling view of the discrete binding pocket comprised of the residues Phe16, Tyr19, Met20, Val23, Val25, Ala33, Phe57, Thr74, Ala75, Asp76, Arg78. The 4-chlorophenyl substituent of compound XVIA is shown bound within this discrete pocket and the hydroxyl group is bound to the Arg-Tyr-Arg residues.

What is claimed is:

1. A method for treating diabetes which comprises administering to a mammalian species in need of treatment a therapeutically effective amount of an aP2 inhibitor, wherein the aP2 inhibitor includes (a) an oxazole or analogous ring selected from the group consisting of a substituted benzoyl or biphenyl-2-oxazole-alkanoic acid derivative, an oxazole derivative, a 2-thio-4,5-diphenyloxazole S-derivative, a phenyl-heterocyclic oxazole derivative, a diaryloxazole derivative, a 4,5-diphenyloxazole derivative, an oxazole carboxylic acid derivative, a phenyloxazolyloxazole derivative, or a 2-(4, 5-diaryl)-2-oxazolyl substituted phenoxyalkanoic acid derivative; and (b) a hydrogen bond donor or acceptor group and (c) an additional substituent which binds within and/or interacts with a discrete pocket within the aP2 protein defined by the amino acid residues designated Phe 16, Tyr 19, Met 20, Val 23, Val 25, Ala 33, Phe 57, Thr 74, Ala 75, Asp 76, Arg 78 in human aP2 (SEQ ID NO: 1).

2. The method as defined in claim 1 wherein the aP2 inhibitor binds to the aP2 protein and inhibits its function and/or its ability to bind free fatty acids.

3. The method as defined in claim 1 wherein said additional substituent in said aP2 inhibitor is hydrophobic in nature.

4. The method as defined in claim 1 in which the through space distance from the hydrogen bond donor/acceptor group and the additional substituent group in said aP2 inhibitor is within the distance of about 7 to about 15 Angstroms.

5. The method as defined in claim 1 wherein Type II diabetes is treated.

6. The method as defined in claim 1 wherein the aP2 inhibitor is employed in the form of a pharmaceutically acceptable salt thereof or a prodrug ester thereof.

7. A method for treating diabetes which comprises administering to a mammalian species in need of treatment a therapeutically effective amount of an aP2 inhibitor, wherein the aP2 inhibitor is selected from the group consisting of:

(I) a substituted benzoylbenzene or biphenyl alkanoic acid derivative having the structure of Formula I: $A(CH_2)_nO-B$ wherein A is a group having the formula

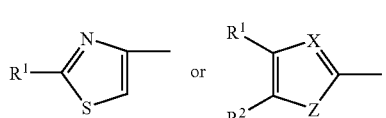

wherein
X is —N—; Z is —S—, or —O—;

$R^1$ is hydrogen, lower alkyl or phenyl;
$R^2$ is hydrogen or lower alkyl; or
$R^1$ and $R^2$ taken together form a benzene ring;
n is 1-2;
B is

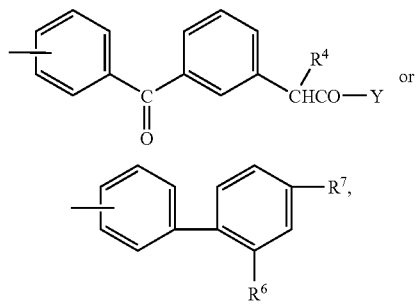

wherein
Y is $OR^5$ or $N(OH)R^8$;
$R^4$ and $R^5$ are each, independently, hydrogen or lower alkyl;
$R^6$ is hydrogen, halo or nitro;
$R^7$ is

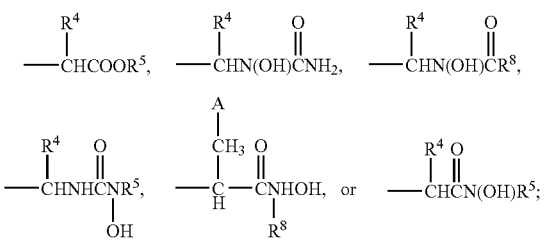

$R^8$ is lower alkyl;
and
pharmacologically acceptable salts thereof;

(II) oxazole derivatives which have the structure of Formula III

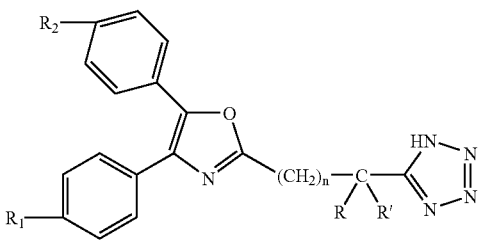

in which

R and R' are identical or different and represent a hydrogen atom or an alkyl radical containing 1 or 2 carbon atoms, $R_1$ and $R_2$ are identical or different and represent hydrogen or halogen atoms or alkyloxy radicals in which the alkyl portion contains 1 to 4 carbon atoms in a straight or branched chain, and n equals 3 to 6 and pharmaceutically acceptable salts thereof;

(III) 2-thiol-4,5-diphenyloxazole S-derivatives which have the structure of Formula III:

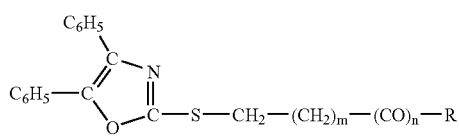

wherein m is 0, 1 or 2, n is 1 and

R represents hydroxy, alkoxy or amino, and pharmaceutically acceptable addition salts thereof;

(IV) azole derivatives of the structure of Formula IV:

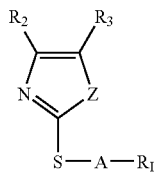

wherein $R_1$ is carboxyl, esterified carboxyl or other functionally modified carboxyl group;

$R_2$ and $R_3$ each are aryl of up to 10 carbon atoms;

A is $C_nH_{2n}$ in which n is an integer from 1 to 10, inclusive;

Z is O or S, and physiologically acceptable salts thereof (V) phenyl-heterocyclic oxazole derivatives which have the structure of Formula V:

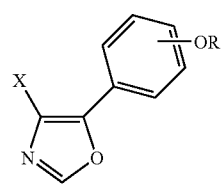

wherein X is

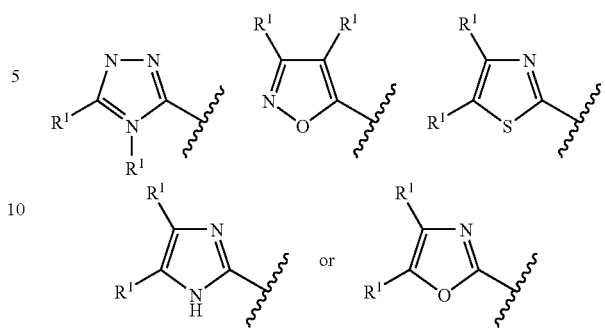

R is $CH_2R^2$;

$R^1$ is Ph or Th;

$R^2$ is

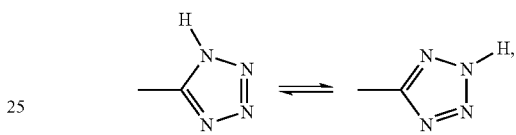

$CO_2R^3$ where $R^3$ is H, or $C_1$-$C_4$ lower alkyl; and pharmaceutically acceptable salt thereof;

(VI) diaryloxazole derivatives having the structure of Formula VI:

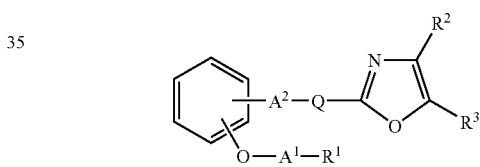

wherein $R^1$ is carboxy or protected carboxy, $R^2$ is aryl, $R^3$ is aryl, $A^1$ is lower alkylene, $A^2$ is bond or lower alkylene and —Q— is

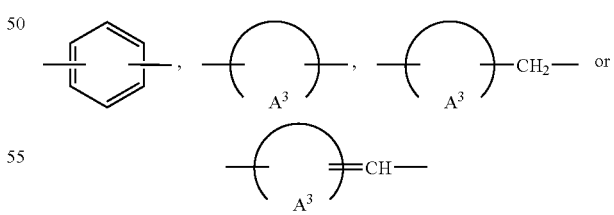

in which

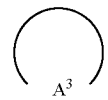

is cyclo (lower)alkane or cycle(lower)alkene, each of which may have substituent(s);

(VII) 4,5-diphenyloxazole derivatives having the structure of Formula VIIA:

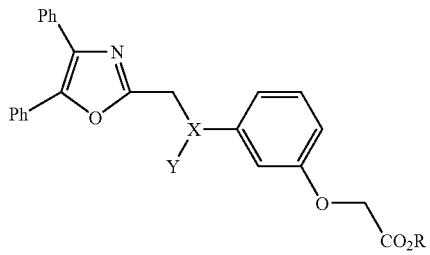

wherein
R is H or $C_1$-$C_5$ lower alkyl,
X is N or CH,
Y is H or $CO_2R^1$, or $COR^2$, provided that when X is CH, Y is not H,
$R^1$ is $C_1$-$C_5$ lower alkyl, or phenylmethyl, and
$R^2$ is $C_1$-$C_5$ alkyl; or of Formula VIIB:

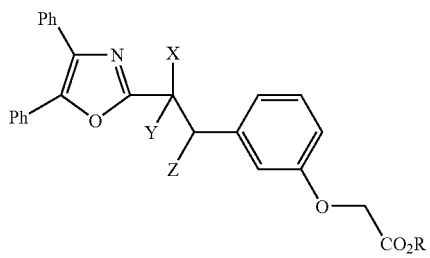

wherein
R is H or $C_1$-$C_5$ lower alkyl,
X is $(CH_2)_n$ or para or meta substituted phenyl wherein the substituent is $OR^2$,
$R^2$ is $C_1$-$C_5$ alkyl, and
n is an integer of 4 to 8, and
pharmaceutically acceptable salts thereof (VIII) oxazole carboxylic acid derivatives having the structure of Formula VIII:

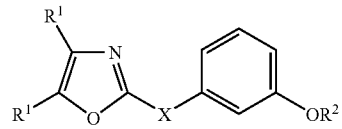

wherein
Y and Z are independently hydrogen or together form a bond;
X is CN, $CO_2R^1$ or $CONR^2R^3$;
R and $R^1$ are independently or together H, Na, or $C_1$-$C_5$ lower alkyl;
$R^2$ and $R^3$ are independently or together H, or $C_1$-$C_5$ lower alkyl; and alkali metal salts thereof;

(IX) phenyloxazolyloxazole derivatives having the structure of Formula IX:

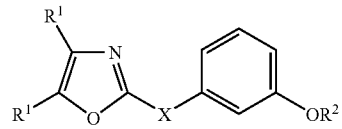

wherein X is

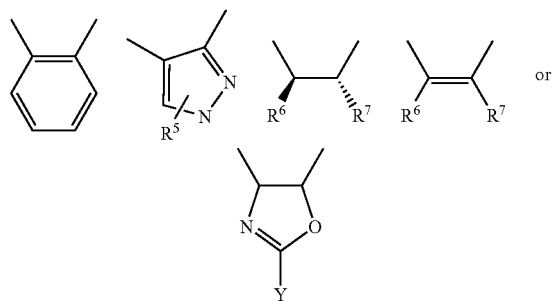

Y is $CH_3$, Ph, or OH, provided that when Y is OH, the compound exists in the keto-enol tautaumerism form

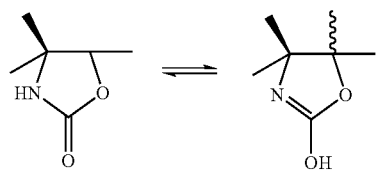

$R^1$ is Ph or Th;
$R^2$ is $CH_2R^3$;
$R^3$ is $CO_2R^4$;
$R^4$ is H or $C_1$-$C_5$ lower alkyl;
$R^5$ is H or $CH_3$;
$R^6$ is OHCHN or $H_2N$; and
$R^7$ is H or OH; and
pharmaceutically acceptable salt thereof;

(X) 2-(4,5-diaryl)-2-oxazolyl substituted phenoxyalkanoic acids and esters having the structure of Formula XA:

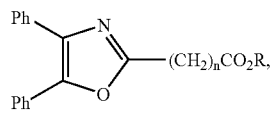

of Formula XB:

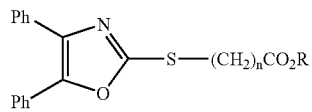

wherein n is 7-9 and R is hydrogen or lower alkyl; or
wherein R is hydrogen, or the alkali metal salt thereof, of Formula XC:

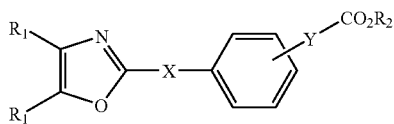 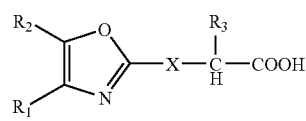

of Formula XD:

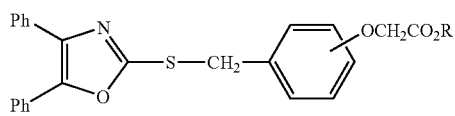

wherein
$R_1$ is phenyl or thienyl;
$R_2$ is hydrogen, lower alkyl or together with $CO_2$ is tetrazol-1-yl;
X is a divalent connecting group selected from the group consisting of $CH_2CH_2$, CH=CH, and $CH_2O$;
Y is a divalent connecting group attached to the 3- or 4-phenyl position selected from the group consisting of $OCH_2$, $CH_2CH_2$ and CH=CH, or when $R_2$ is hydrogen, an alkali metal salt thereof;

(XI) substituted 4,5-diaryl heterocycles having the structure of Formula XI:

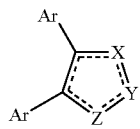

wherein
each group Ar is the same or different and is optionally substituted phenyl or optionally substituted heteroaryl;
X is nitrogen;
Y is $C(CH_2)_nA$;
Z is oxygen, and the dotted line indicates the optional presence of a double bond so as to form a fully unsaturated heterocyclic ring;
n is 4 to 12; and
A is $CO_2H$ or a group hydrolysable to $CO_2H$, 5-tetrazolyl, $SO_3H$, $P(O)(OR)_2$, $P(O)(OH)_2$, or
$P(O)(R)(OR)$ in which R is hydrogen or $C_{1-4}$alkyl; and pharmaceutically acceptable salts thereof;
(XII) compounds which have the structure of Formula XII:

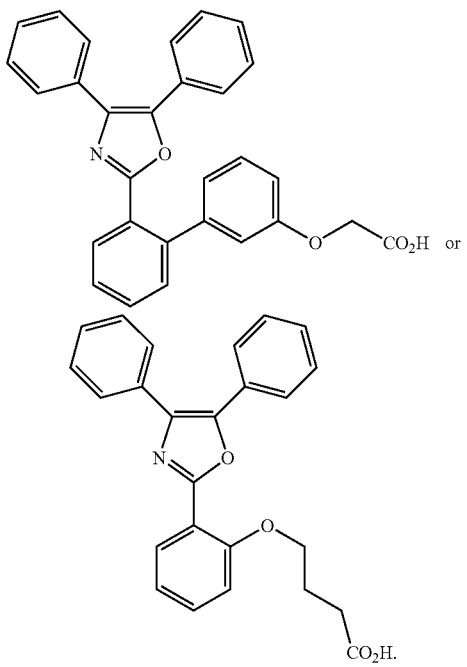

wherein X is O or S;
$R_1$ is H, phenyl or phenyl substituted with F, Cl or Br or alkoxy,
$R_2$ is H, alkyl, phenyl or phenyl substituted with F, Cl or Br or alkoxy, and
$R_3$ is H or alkyl.

8. The method as defined in claim 1 wherein the aP2 inhibitor has the structure

* * * * *

UNITED STATES PATENT AND TRADEMARK OFFICE
CERTIFICATE OF CORRECTION

PATENT NO. : 7,390,824 B1  Page 1 of 2
APPLICATION NO. : 09/391053
DATED : June 24, 2008
INVENTOR(S) : Robl et al.

It is certified that error appears in the above-identified patent and that said Letters Patent is hereby corrected as shown below:

On the Title Page, Item (75) Inventors: should read:
-- (75) Inventors: Jeffrey A. Robl, Newtown, PA (US);
Rex A. Parker, Titusville, NJ (US);
Scott A. Biller, Hopewell, NJ (US);
Haris Jamil, Newtown, PA (US);
Bruce L. Jacobson, Mercerville, NJ (US);
Krishna Kodukula, Princeton, NJ (US);
Gokhan Hotamisligil, Wellesley, MA (US) --.

On Title Page, Item (73) Assignees: should read:
-- (73) Assignees: Bristol-Myers Squibb Company, Princeton, NJ (US); President and Fellows of Harvard College, Cambridge, MA (US). --.

Column 26, Claim 7, lines 55-60, please delete " 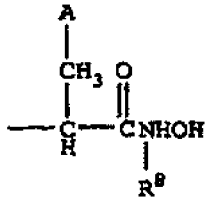 " and insert

-- 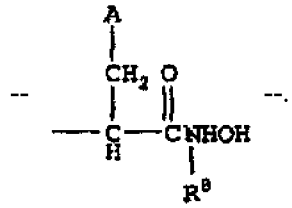 --.

Column 26, Claim 7, line 67, please delete "III" and insert -- II --.

UNITED STATES PATENT AND TRADEMARK OFFICE
CERTIFICATE OF CORRECTION

PATENT NO. : 7,390,824 B1
APPLICATION NO. : 09/391053
DATED : June 24, 2008
INVENTOR(S) : Robl et al.

It is certified that error appears in the above-identified patent and that said Letters Patent is hereby corrected as shown below:

Column 30, Claim 7, line 56, please delete "of" and insert -- or --.

Column 31, Claim 7, line 9, please delete "of".

Signed and Sealed this

Second Day of December, 2008

JON W. DUDAS
*Director of the United States Patent and Trademark Office*